United States Patent [19]

Ferrell et al.

[11] Patent Number: 5,750,130
[45] Date of Patent: May 12, 1998

[54] PRESTICIDE COMPOSITIONS

[76] Inventors: Paul Ferrell, 5316 Oakwood Dr., Sheffield, Ohio 44054; Alice P. Hudson, 184 Sims Creek La., Jupiter, Fla. 33458

[21] Appl. No.: 694,871

[22] Filed: Aug. 9, 1996

Related U.S. Application Data

[63] Continuation of Ser. No. 385,104, Feb. 7, 1995, abandoned.

[51] Int. Cl.⁶ .................................................. A01N 25/12
[52] U.S. Cl. .......................... 424/417; 424/409; 424/418; 424/419; 424/420; 424/421
[58] Field of Search ................................ 424/408, 409, 424/417–421; 71/64.02, 64.03, 64.07

[56] References Cited

U.S. PATENT DOCUMENTS

| | | | |
|---|---|---|---|
| 3,342,577 | 9/1967 | Blouin | 71/3 |
| 3,617,246 | 11/1971 | Duytjes | 71/79 |
| 3,849,105 | 11/1974 | Woods | 71/65 |
| 3,980,463 | 9/1976 | Muramoto | 71/86 |
| 4,015,970 | 4/1977 | Hennant | 71/11 |
| 4,042,366 | 8/1977 | Fersch | 71/29 |
| 4,398,943 | 8/1983 | Kajioka et al. | 71/92 |
| 4,804,403 | 2/1989 | Moove | 71/28 |
| 4,871,392 | 10/1989 | Morgan et al. | 71/121 |
| 4,874,425 | 10/1989 | Kimpara et al. | 71/121 |
| 5,089,041 | 2/1992 | Thompson et al. | 71/64.11 |
| 5,186,732 | 2/1993 | Thompson et al. | 71/64.11 |
| 5,283,231 | 2/1994 | Morgan et al. | 504/148 |
| 5,326,573 | 7/1994 | Antfang | 424/490 |

FOREIGN PATENT DOCUMENTS

| | | | |
|---|---|---|---|
| 7411591 | 12/1990 | Australia | C05G 5/00 |
| 01157492 | 6/1989 | Japan | C05G 3/02 |
| 01157493 | 6/1989 | Japan | C05G 3/02 |
| 0360486 | 3/1991 | Japan | C05G 3/00 |

*Primary Examiner*—Neil S. Levy

[57] ABSTRACT

Granular pesticide compositions wherein a pesticide material is applied to a granular substrate using a carrier composition which provides improved adhesion of the pesticide to the substrate and abrasion resistance. The carrier composition may also provide controlled release of the pesticide.

8 Claims, No Drawings

PRESTICIDE COMPOSITIONS

This is a continuation of application Ser. No. 08/385,104 filed Feb. 7, 1995, now abandoned.

BACKGROUND OF THE INVENTION

1. Field of the Invention

This invention relates to pesticide compositions in which the pesticides and a carrier material are applied to a substrate, said carrier material providing improved adherence of the pesticide to the substrate and improved attrition resistance. The carrier compositions may also be used to control the rate of release of the pesticide to the environment.

2. Description of the Prior Art

It is often desirable to incorporate materials with herbicidal, insecticidal or fungicidal properties onto the surface of granular fertilizers or inert granular carriers for agricultural, horticultural, and other pest control applications. Many of these pesticides are solid materials which adhere poorly to the surfaces of the granular materials. To assure uniform application of the pesticides at effective levels the pesticide materials must be uniformly distributed in the compositions. Thus they are used in the form of fine powders, or dissolved in solvents and applied as solutions. When the powdered pesticides do not adequately adhere to the surface of the granular materials, in the course of mixing, transporting and applying the compositions, the pesticides tend to separate as a dust, creating both an uneven distribution of pesticide in the formulation, and an airborne dust problem.

When the pesticides are applied from solvent solutions, the solvents may evaporate causing the herbicide materials to crystallize as fragile, easily abraded particles on the surfaces of the substrates.

It is also desirable to control the rate of release of the pesticide to the environment under the conditions of use. Certain pesticides such as preemergent herbicides are usually most effective if released over a period of time; others such as certain insecticides are most effective if released immediately.

When applying liquid pesticides to granular substrates, it is important that they be evenly distributed on the surfaces of the granules to assure uniform application of the pesticide in use. If the liquid pesticides are applied to the substrate without dilution as a very small particle spray necessary to assure uniform distribution, the airborne droplets may create a serious health and environmental hazard. To improve the distribution of the liquid pesticides, solvents can be used as diluents, but the solvents do not always mitigate the airborne hazard and may even contribute to it. Liquid pesticides may also be applied to substrates in the form of water emulsions. The water can be undesirable in that it may cause the substrate to dissolve or cake. Thus a method of application that uniformly distributes the pesticides on the surface of the granules without creating an environmental hazard or causing caking of the substrate is needed.

OBJECTS

The principal object of this invention is the provision of efficacious granular pesticidal materials.

A further object is the provision of granules in which the active pesticidal material uniformly adheres to the granule surfaces.

Another object is the provision of pesticide containing granules from which the pesticide is not separated during mixing, transportation, or application.

A further object is the provision of pesticide containing compositions in which the rate of release of the pesticide to the environment can be controlled.

SUMMARY OF THE INVENTION

These objects are attained by the provision of pesticidal compositions in which the pesticide and a carrier composition are applied to the surface of an active or inert granular substrate.

DESCRIPTION OF THE PREFERRED EMBODIMENTS

The term "pesticide" in the context of this invention refers to any agent used to destroy insects, arachnids, fungi, unwanted vegetation, rodents, and other pests. Pesticides particularly useful in agricultural and horticultural applications include herbicides, insecticides, fungicides, and rodenticides. Pesticides which are useful in the composition of this invention are those which are solid materials or low volatility liquids at temperatures at which they are sold and used. Some examples of pesticides which may be used in the compositions of this invention include:

| | |
|---|---|
| Atrazine | Fosetyl aluminum |
| Diazinon | Methoxychlor |
| Metsulfuron-methyl | 3-Amino-s-triazole |
| Iprodione | Dicamba |
| Bentazon/Bentazone | Triadimefon |
| Bendiocarb | Benefin |
| Benomyl | Bensulide/Betasan |
| Acifluorfen | Boric Acid |
| Bromoxynil | Butachlor |
| Cacodylic acid | 4-Cyclohexene-1,2-dicarboximide N-[(trichloromethyl)thio]- |
| Carbaryl | Chlorpyrifos |
| Halosulfuron-methyl | Copper sulfate |
| Copper oxide | Flurprimodol |
| 2,4-Dichlorophenoxyacetic acid | Monosodium methylarsenate |
| Dacthal (DCPA) | Napropamide/Devrinol |
| Dichlorprop | Fenoxaprop-ethyl |
| Alachlor | Aldicarb |
| Hydramethylnon | Bacillus thuringiensis var. kurstaki |
| Prodiamine | Baytan |
| Butocarboxim | Chl orfl orenol |
| Chlorothalonil | Chlorsulfuron |
| 2,4-Dichlorophenoxybtityric acid | Dichlorprop-P |
| Disulfoton | Disodium methylarsenate |
| Trichlorfon | Dyfonate |
| s-Triazine, 2,4-dichloro-6-(o-chloroanilino)- | Endothion |
| Ethitinol | |
| Ethoprop | Ethofumesate |
| Ferrous sulfate | Fenoxaprop-ethyl |
| Glyphosate | Isoxaben |
| Imidacloprid | oxyfluorfen |
| Isazofos | Flutriafol |
| 2-metyl 4-chlorophenoxyacetic acid | Isofenphos |
| | Potassium 2-(2methyl-4-chlorophenoxypropionate |
| Mecoprop | Metalaxyl |
| Methiocarb | Oxadiazon |
| Paclobutrazol | pentachloronitrobenzene |
| Permethrin | Pramitol |
| Primicid | Propachlor |
| Propanil/Quinclorac | Pendimethalin |
| Fenarimol | Tolclofos-methyl |
| Imazaquin | 1-(2-Methylcyclohexyl)-3-phenylurea |
| Simazine | Sonalan/Ethalfluralin |
| Sulfur | Oryzalin |
| Thiophanate-methyl | Thiram |
| Triclopyr | Trifluralin |
| Vinclozolin | Fonofos |
| Carbamic acid, ethylenebisdi- | Malathion |

| thio-, manganese zinc complex | |
|---|---|
| Cyfluthrin | Acephate |
| Bromadil | Dichlobenil |
| Dithiopyr | |

Mixtures of pesticides may also be used when the combined effects of two or more products are desirable, provided any one does not interfere with the activity of the others.

Substrate compositions can be active materials such as fertilizer particles, or inert materials such as limestone or clay minerals. They may be porous or non-porous. The size of the substrate granules is not critical to the invention, but it is preferred that they be large enough so that they are not a dust hazard of themselves, yet of an adequately small size so as to present a sufficiently large surface area for the adhesion of an effective level of the pesticide-carrier compositions, and so that they be applied in the standard equipment used for the intended applications. Preferred granules are from about 0.2 to 10 mm in diameter. Mixtures of suitable substrate materials may also be used.

Substrate compositions can be commercial particulate fertilizers which are produced and marketed in several different particle types, i.e., granular, pelletized and prilled fertilizers, and may be formed of inorganic substances, organic substances, or combinations thereof. Such particulate fertilizers can be made of a single component, e.g., urea, sulfur coated urea, ammonium nitrate, potassium chloride, potassium sulfate, monoammonium phosphate, diammonium phosphate, sewage sludge, manure, etc., or of multiple components often mixed with inert water soluble or water insoluble materials as in common fertilizers designated 6-6-6, 4-6-4, 10-10-10, 20-20-5, 14-16-0, 5-20-20 and the like.

Substrate compositions can also be inorganic or organic inert granular materials. Suitable inorganic substrates are for example limestone, clay minerals, gypsum, brick scrap, fly ash, vermiculite, diatomaceous earth, and the like.

Suitable organic substrates include cellulosic materials such as recycled paper pulp, corn cobs, peanut hulls, rice hulls, walnut shells, pecan shells, coconut shells, sawdust, and compost; and synthetic organic materials such as perlite.

The carrier materials are characterized by being cohesive solids at temperatures below about 50° C., and low viscosity liquids in the molten state, by having melting points low enough so that in their molten state they do not thermally degrade the pesticide or substrate materials, and by being nonreactive with the pesticide and substrate compositions.

The carrier materials provide improved adhesion of the pesticide to the substrate granules and improved abrasion resistance. If desired they can be formulated to also provide controlled release of the pesticide to the environment. They may also provide protection from atmospheric humidity to moisture sensitive pesticides and substrates, and may be formulated to provide protection from ultraviolet radiation.

Suitable carrier materials include petroleum based and synthetic hydrocarbon materials, including waxes which have melting points (by ASTM D-127) preferably from about 50° C. to about 120° C. and melt viscosities (by ASTM D-445) at 120° C. preferably less than about 200 centistokes. Examples of suitable petroleum waxes include microcrystalline waxes which have melting points from about 65° to about 100° C., paraffin waxes which have melting points from about 50° to about 100° C., and slack waxes which have melting points from about 50° to about 80° C.

Examples of synthetic hydrocarbon waxes include alpha olefins with about 24 or more carbon atoms, and polyethylenes with molecular weights of about 1000 or lower.

Other suitable carriers include vegetable and animal derived waxes and modifications thereof which have melting points preferably from about 50° C. to about 120° C. Examples include triacyl glycerides produced by the partial or complete hydrogenation of natural fats and oils derived from lard oil, beef tallow, fish oils, corn oil, palm oil, coconut oil, peanut oil, rapeseed oil, soybean oil, canola oil, sesame seed oil, and sunflower seed oil.

Also included are natural waxes, of which carnauba wax, montan wax, beeswax, ricebran wax, and ozokerite are representative.

The carrier compositions optionally contain wax soluble surfactants which modify the rate at which the pesticide is released to the environment by modifying the hydrophilicity of the carrier materials. The water dispersibility of the carrier materials and thus the rate at which the pesticides are released when the compositions encounter moist conditions, can be controlled by the level of and the water solubility of the surfactant materials added. These wax soluble surfactants must not interfere with the activity of the pesticides. Suitable wax soluble surfactants can be nonionic surfactants with Hydrophilic Lipophilic Balance (HLB) values of less than about 10. Examples include glyceryl monostearate, glyceryl distearate, sorbitan trioleate, propylene glycol monostearate, sorbitan monostearate, tallow amine condensed with 2 moles of ethylene oxide per mole of amine, and $C_{18-26}$ alcohols condensed with from about 2 to about 10 moles of ethylene oxide per mole of alcohol.

Suitable wax soluble surfactants can also be organic amine salts of acidic anionic surfactants such as fatty acids, phosphate esters, sulfates or sulfonates. Examples include morpholinium cocoate, diisopropanolammonium tallate, N,N-dibutylethanolammonium $C_{12}$alkylbenzenesulfonate, and dibutylammonium mono-$C_{18}$alkylphosphate.

Mixtures of carrier materials may be used. The carrier compositions may also contain minor amounts of solvent materials to facilitate the application of the carrier-pesticide compositions.

Other adjuvants which are commonly used in fertilizer compositions and/or pesticide compositions, such as micronutrients, dyes, flow aids, and the like, can be incorporated into the compositions of this invention.

This invention is also directed to methods for producing the pesticide containing granules. The compositions of this invention can be produced by a variety of procedures, depending on the particular pesticides, carriers, substrates, levels of application and other aspects of the final composition.

In a currently preferred procedure, the pesticide material is mixed with the molten carrier composition as a slurry or as a homogeneous mixture, and this mixture is added preferably as a spray to the substrate material. The pesticide-carrier mixture can be added while the substrate is being agitated in a tumbling mixer such as a Munson mixer or a Continental mixer, or in a pan granulator, or it can be added to a falling curtain of the substrate in a rotating drum, or added while the substrate material is being transported on a belt conveyor.

In another suitable procedure the substrate and the fine particles of pesticide material are mixed in a suitable mixer, and the carrier composition is added as a molten material, preferably as a spray. This is preferably accomplished in a tumbling mixer or other mixer that assures uniform distribution of the pesticide material.

In another suitable procedure the substrate material is mixed with the molten carrier material, and while the carrier is still in a liquid or semisolid state the pesticide material is applied with suitable mixing to imbed the material into the carrier compositon.

The process can be carried out at a variety of temperatures depending on the particular materials being used. The carrier composition is preferably applied as a molten material. If the carrier composition is applied as a sufficiently small particle spray, it can be applied to the substrate materials at ambient temperatures. Alternatively the substrate can be heated to a temperature sufficient to melt the carrier material and allow it spread over the substrate surfaces.

The following examples are provided to illustrate the preferred compositions, the preferred method of preparation, and comparative evaluations. In these examples all percentages are by weight based on the total weight of all components in the described compositions.

EXAMPLE 1

A wax carrier composition was prepared by melting together 75% slack wax (congealing point 68° C., 15% oil content) and 25% hydrogenated tallow (iodine value 2).

19.5 lb of 90% active Pendimethalin (a preemergent herbicide) was melted together with 12.5 lb of the above described wax carrier at 82° C. This molten mixture was sprayed onto 2000 lb of a 22-4-4 mixed granular fertilizer while agitating in a Munson mixer.

EXAMPLE 2

A surfactant-wax carrier composition was prepared with the following composition:

75% slack wax (congealing point 68° C., 15% oil content)
25% morpholinium cocoate 19.5 lb of 90% active Pendimethalin was melted together with 12.5 lb of the above described surfactant-wax carrier at 82° C. This molten mixture was sprayed onto 2000 lb of a 22-4-4 mixed granular fertilizer while agitating in a Munson mixer.

EXAMPLE 3 (COMPARATIVE)

19.5 lb of 90% active Pendimethalin was dissolved in 12.5 lb of deodorized kerosine at 82° C. This molten mixture was sprayed onto 2000 lb of a mixed granular fertilizer while agitating in a Munson mixer.

To measure the tendency of the herbicide to separate from the fertilizer granules, a standard Ro-Tap sieve analysis was performed on the herbicide-fertilizer compositions of Examples 1–3. The results were as follows:

|  | % of total fertilizer composition passing throuah a 60 mesh sieve |
|---|---|
| Example 1 | ≦0.1 |
| Example 2 | ≦0.1 |
| Example 3 | 0.8 |

To measure the release of the herbicide under moist conditions in the environment, 20 g of the herbicide-fertilizer compositions of Examples 1–3 were added to 50 ml of water and shaken on a laboratory shaker for 15 minutes. The water slurries were screened through a 20 mesh sieve and the pendimethalin content of the retained portion was measured. The results of this analysis were as follows:

|  | % of herbicide not released from granules |
|---|---|
| Example 1 | 49 |
| Example 2 | 39 |
| Example 3 | 45 |

Thus the addition of the surfactant in Example 2 increases the rate of release of the herbicide.

To measure the abrasion resistance of the herbicide-fertilizer compositions of Examples 1–3, 20 g of product was mixed with 50 g of sand and tumbled in a ball mill for 30 minutes. The product were separated from the sand by screening. Both the product and the sand was analyzed for pendimethalin. The results of these analyses were as follows:

|  | % of herbicide retained on fertilizer |
|---|---|
| Example 1 | 95 |
| Example 2 | 94 |
| Example 3 | 58 |

Thus the composition of Examples 1 and 2 are much more resistant to abrasion than the material without the carrier compositions.

To demonstrate the efficacy of the herbicide in the herbicide-fertilizer compositions of Examples 1–3, greenhouse trays containing a normal potting mix were seeded with twice the normal application rate of ryegrass and crabgrass, and divided into 3 inch square plots. One particle of the products from Examples 1, 2, and 3 were placed in the center of each of the plots, and the trays were sprayed with ¾ inch of water and maintained moist by watering from the bottom of the tray. The trays were maintained under artificial lighting. After the grass seeds had germinated, the sphere of influence of the herbicide was measured from the particle to the point of grass germination. No significant differences were noted between the composition of Example 3 and the compositions of Examples 1 and 2, indicating that the carrier compositions do not interfere with the herbicidal activity of the pendimethalin.

EXAMPLE 4

The following carrier compositions were prepared, mixed with pendimethalin, and applied to the fertilizer composition in the ratios and by the methods of Example 1.

100% Hydrogenated tallow (iodine value 2)

100% Slack wax (congealing point 68° C., 15% oil content)

50% Slack wax (congealing point 68° C., 15% oil content)

50% $C_{22}$ alcohol+10 moles of ethylene oxide

50% Hydrogenated tallow (iodine value 2)

50% $C_{22}$ alcohol+10 moles of ethylene oxide

100% $C_{22}$ alcohol

100% Glycerol mono- and distearate, 52% mono

75% Slack wax (congealing point 68° C., 15% oil content)

25% coconut fatty acid salt of di-n-butylaminoethanol

EXAMPLE 5

Using any of the carrier compositions of Examples 1, 2, and 4, and the application procedure of Example 1, the following pesticidal compositions can be prepared:

| Pesticide | % of active pesticide on substrate | Substrate |
|---|---|---|
| Treflan | 0.5–5 | Limestone granules |
| Dursban | 0.4–3 | Kaolin granules |
| Iprodione | 0.5–2.5 | Paper pulp granules |
| Triadimefon | 0.5–1.5 | Limestone granules |
| Diazinon | 1.0–3.4 | Peanut hull granules |
| Carbaryl | 1.0–6.3 | Attapulgite clay granules |
| Dicamba | 0.06–1.0 | Vermiculite |

The invention can be embodied in other forms without departing from the spirit or essential attributes thereof. Particularly it will be appreciated by those skilled in the art that alternative carriers, pesticides, and substrates to those disclosed herein could have utility in the invention. Reference should therefore be had to the following claims, rather than to the foregoing specification to determine the scope of the invention.

The Embodiments of the invention in which an exclusive property or priviledge is claimed are defined as follow:

1. A pesticide product comprising at least one granular substrate chosen from the group consisting of granular fertilizers and inert granular materials, said granular substrate having applied to the surface thereof a coating comprising at least one pesticidal compound chosen from the group consisting of dinitroaniline herbicides, and at least one carrier which is an abrasion resistant solid at temperatures below about 50° C. and a liquid with viscosity less than about 200 centistokes above about 120° C., chosen from the group consisting of waxes, wax soluble surfactants, and mixtures thereof, wherein the pesticidal compound is from about 0.05 to about 7% by weight of the total composition, and the weight ratio of the pesticidal compound to the carrier is from about 40 to 60 to about 70 to 30.

2. The pesticidal product of claim 1 wherein the pesticidal compound and the carrier are a homogenous mixture applied to the substrate.

3. The pesticidal product of claim 1 in wherein the pesticidal compound and the substrate are a physical mixture to which a carrier has been applied.

4. The pesticidal product of claim 1 wherein the pesticidal compound is embedded in the carrier and the carrier surrounds the substrate.

5. The pesticidal product of claim 1 wherein the carrier comprises a wax soluble surfactant.

6. The pesticidal product of claim 1 wherein the substrate is a granular fertilizer.

7. The pesticidal product of claim 1 wherein the substrate is an inert granular material.

8. The pesticidal product of claim 1 wherein the granular substrate is a fertilizer, the pesticidal compound is pendimethalin, and the carrier is a wax with a melting point above about 50° C.

* * * * *